United States Patent [19]
Butland et al.

[11] Patent Number: 6,030,657
[45] Date of Patent: Feb. 29, 2000

[54] LABELING TECHNIQUE FOR COUNTERING PRODUCT DIVERSION AND PRODUCT COUNTERFEITING

[75] Inventors: Charles L. Butland, Playa Del Rey, Calif.; Breffni Baggot, Manchester, Conn.

[73] Assignee: DNA Technologies, Inc., Los Angeles, Calif.

[21] Appl. No.: 09/003,848

[22] Filed: Jan. 7, 1998

Related U.S. Application Data

[63] Continuation-in-part of application No. 08/794,625, Feb. 3, 1997, abandoned, which is a continuation-in-part of application No. 08/333,077, Nov. 1, 1994, Pat. No. 5,599,578.

[51] Int. Cl.$^7$ ....................................................... B41M 3/14
[52] U.S. Cl. .............................. 427/7; 427/157; 427/160; 427/256; 427/288; 427/384; 106/31.32; 252/301.4 R; 252/301.16
[58] Field of Search ............................... 427/7, 157, 160, 427/256, 288, 384; 106/37.32; 252/301.4 R, 301.16

[56] References Cited

U.S. PATENT DOCUMENTS

| | | | |
|---|---|---|---|
| 3,886,083 | 5/1975 | Layer | 427/7 |
| 4,387,112 | 6/1983 | Blach | 427/7 |
| 5,136,812 | 8/1992 | Lebacq | 427/7 |

*Primary Examiner*—Janyce Bell
*Attorney, Agent, or Firm*—Mueller and Smith, LPA

[57] ABSTRACT

The present invention is directed to a method for labeling an object for its identification in order to counter product diversion and product counterfeiting. This method includes providing an encapsulated biologic marker labeled with an agent that emits selected detectable wavelengths of energy when exposed to infrared radiation (IR), and associating the labeled marker with the object, whereby, the object to be identified can be exposed to IR and emitted select wavelengths of energy from said agent detected. The agent can be an upconverting phosphor, a lanthenide ion (bound to a naphthalene group), or other chemical that emits selected detectable wavelengths of energy when exposed to infrared radiation (IR). Biologic markers include, inter alia, one or more of a protein, a nucleic acid sequence, an antibody, a polypeptide, or an antigen. The encapsulant for the biologic marker preferably is casein which has been cross-linked with itself.

23 Claims, No Drawings

LABELING TECHNIQUE FOR COUNTERING PRODUCT DIVERSION AND PRODUCT COUNTERFEITING

CROSS-REFERENCE TO RELATED APPLICATIONS

This application is a continuation-in-part of U.S. application Ser. No. 08/794,625, filed Feb. 3, 1997, now abondoned, which is a continuation-in-part of U.S. application Ser. No. 08/333,077, filed Nov. 1, 1994, now U.S. Pat. No. 5,599,578.

BACKGROUND OF THE INVENTION

The present invention relates to the labeling of objects for verifying authenticity and more particularly to the use of selectively-perceptible marks for labeling of objects. Authenticity implies both that the goods are genuine and that they are in the proper channels of commerce. If the goods are not genuine, then product counterfeiting has occurred and the present invention presents the ability to determine whether or not goods are genuine. If the goods have been diverted from their intended channel of commerce by, for example, entering into a country where the goods are prohibited, for example, by contract or by law, then the goods have been subject to product diversion. Again, the present invention presents the ability to determine whether genuine goods have been improperly diverted. Finally, diverted goods also comprehends genuine goods which have been stolen and the identity of the goods is at issue.

Many objects require verification for authentication purposes. Such objects include paintings, sculptures, cartoon cells, sports and other collectibles, and like works of art; video cassette recorders, televisions, and like household objects; and computers; printers, and like office and business equipment. Other instances of identification in order to verify ownership, include, for example, records, audio and video tape cassettes, computer software recorded on floppy disks or diskettes, perfumes, designer clothes, handbags, briefcases, cartoon cells, automobile/airplane parts, securities (e.g., stock certificates), wills, identification cards (driver's licenses, passports, visas, green cards), credit cards, smart cards, and like objects. Many industries have been plagued by a flagrant piracy explosion over the past decade involving many of the foregoing products. Often, these objects have no serial number or other unique means of identification, or the number can be removed easily following a theft. Alternatively, counterfeiting of such objects has become a thriving business and the need to identify authentic from counterfeit objects is of great importance.

In a related, but different, scenario, genuine goods are limited to being shipped and sold in selected jurisdictions (e.g., countries), for example, by law or by contract. When genuine goods are diverted to countries where their presence is not authorized, then "product diversion" has occurred. Product diversion can lead to, inter alia, price inequities in certain markets as well as loss of exclusivity by some manufacturers or distributors. This situation often is referred to as "gray market" goods. Since the goods are genuine, it is quite difficult to determine whether the goods have been improperly diverted. This is especially true for a variety of goods such as, for example, clothing.

In U.S. Pat. No. 5,599,578 (cited above), there is disclosed a technique for labeling objects for their identification and/or authentication involving the use of a combination of a mark visible to the naked eye and a mark invisible to the naked eye. The invisible mark or component of the system is one or more of an ultraviolet radiation (UV) dye, an infrared (IR) dye, an ink that displays a selected measurable electrical resistivity, or a biologic marker which may be a protein, amino acid, DNA, polypeptide, hormone, or antibody.

One problem associated with the use of biologic markers that was discovered during the course of developing the present invention is that some inks degrade the DNA marker. Heretofore, the art has not recognized that lithographic inks degrade DNA. Thus, the present invention is addressed to, inter alia, utilizing biologic markers in ink formulations for countering product diversion and product counterfeiting and to the use of phosphors associated with such biologic markers.

DISCLOSURE OF THE INVENTION

The present invention in one aspect is directed to a method for labeling an object for its identification. This method includes providing a biologic marker labeled with an agent that emits selected detectable wavelengths of energy when exposed to infrared radiation (IR), and associating the labeled marker with the object, whereby, the object to be identified can be exposed to IR and emitted select wavelengths of energy from said agent detected. The agent can be an upconverting phosphor, a lanthenide ion (bound to a naphthalene group), or other chemical that emits selected detectable wavelengths of energy when exposed to infrared radiation (IR).

Another aspect of the present invention is a method for identifying an objec. This method includes the steps of first exposing an object presented for identification to infrared radiation (IR). Next, a detector is placed adjacent to the object. The detector is capable of detecting a select wave length of energy which is emitted by an up-converting phosphor responsive to IR or to a lanthenide ion bound to a naphthalene group. The phosphor or lanthenide ion is attached to a biologic marker capable of being affixed to the object. The object is identified by the presence or absence of the select wavelength of energy detected or not detected by the detector. The biologic also can be a DNA fragment encoded to convey information useful in confirming the identification of the object. The presence or absence of the up-converting phosphor or lanthenide ion can be a trigger releasing the detector to scan a bar code of other scanable code utilizing conventional bar code reader engines.

The materials are encapsulated in an encapsulant that is resistant to the environment in which the materials are used such as, for example, an ink formulation. However, the encapsulant can be opened (e.g., by selective dissolving) and the materials inside (e.g., biologic, IR emittant, etc.) determined. A presently preferred encapsulant is casein which has been self cross-linked to provide resistance to hydrophobic ink formulations in which it desirably is placed.

Advantages of the present invention include a simple, yet reliable means for labeling objects for identification. Another advantage is that a portion of the label is not perceptible to people absent the application of special techniques in order to determine the presence of such labels. Another advantage is that the label can last for an almost indefinite period of time. A yet further advantage is the ease and versatility for identification which is afforded by the present invention. Another advantage is the ability to encrypt the biologics for embedding information, such as point of origin, for product diversion. These and other advantages will become readily apparent to those skilled in the art based upon the disclosure contained herein.

DETAILED DESCRIPTION OF THE INVENTION

Once an object is identified and the identification verified, it can be labeled in accordance with the inventive technique disclosed herein so that its authentication at a later date is materially enhanced. For present purposes, "permanent" as applied to the present labeling technique of an object means that the label is incapable of being removed from the object in the ordinary course of intended handling and usage of the object for a time adequate for identification and/or verification of the object to occur and/or is placed on the object at a location that is seldomly, if ever, accessed by the user in the ordinary course of using the object. For some objects, it may be desirable that the label remain affixed to the object and identifiable for many years. Such objects would include works of art, household and business appliances, machinery, automobiles, automobile parts, records, video audio tape cassettes, computer software diskettes, and the like. It is conceivable that some objects would require verification for only a limited time (e.g., for several days to several months); however, it is believed that extended verification time periods will find greater acceptance in the market place.

Biologic markers, such as amino acids and proteins are disclosed in U.S. Pat. No. 5,194,289, cited above. Such biologic materials can be profiled by gas chromatography which creates a standard for later comparison with a small (e.g., nanogram) sample of ink from a stolen object, a counterfeit object, or a diverted genuine object, which objects have been labeled in accordance with the precepts of the present invention. Additionally, U.S. Pat. No. 5,139,812 discloses the use of nucleic acid sequences in ink for identifying an object with a probe. U.S. Pat. No. 4,880,750 discloses the use of individual-specific antibodies (e.g., in an ink) for identification of security documents. U.S. Pat. No. 4,441,943 uses synthetic polypeptides for labeling explosives. British Patent No. 2,209,831 proposes to label objects with a nucleic acid, antibody, or antigen. U.S. Pat. No. 5,451,505 uses nucleic acids as taggants. U.S. Pat. No. 5,429,952 proposes to associate hapten with a product and then later detecting the presence of hapten with a complementary binding member and, thus, identify the product. MHC (major histocompatibility complex is yet another biologic marker suitable for use in the present invention. Thus, the term "biologic marker" should be construed broadly to include biologic materials (natural and synthetic, whole or fragments, naturally occurring, synthetic, and/or modified) for use in accordance with the precepts of the present invention. The disclosures of these citations are expressly incorporate herein by reference.

Such techniques also are not readily perceptible without the aid of special equipment and/or chemicals which develop the presence of such markers. For present purposes, such markers are unique and not easily (if at all) replicated by the forger or counterfeiter. The foregoing biologic markers may be incorporated into a visible (of the same or a different color from the object or product being marked) or an invisible ink for use in labeling objects. It should be understood also that such biologic markers can be native or can be synthetic, including fragments, single chains, and a variety of additional forms currently developed or yet to be developed. It may even be feasible to radiolabel some biologic or other markers and determine their presence thereby.

Moreover, DNA (RNA, antibodies, antigens, and like biologics) can be used to encrypt and transport information in situ. The encoded messenger DNA (or mDNA) would be virtually impossible to detect and decode without prior knowledge of its presence and composition. A quantity in the femtogram range or just a few bacterial cells or bacteriophage particles would be sufficient to encode a complex message.

The biologic molecules may consist of a single biomolecule which may have multiple traits (for example, size and weight) identifiable with the source of the product and/or destination of the product. Alternatively, the biomolecule can consist of a set of biomolecules (e.g., plasmids or fragments of nucleic acid or proteins), each differing in a single trait (e.g., size). Table 1, below, depicts the number of possible combinations which can be derived from a given number of DNA segments.

TABLE 1

| Number of DNA Segments | Number of Combinations |
|---|---|
| 2 | 3 |
| 3 | 7 |
| 4 | 15 |
| 5 | 31 |
| 6 | 63 |
| 7 | 120 |
| 8 | 247 |
| 9 | 502 |
| 10 | 1,023 |
| 11 | 2,047 |
| 12 | 4,095 |
| 13 | 8,191 |
| 14 | 16,381 |
| 15 | 32,767 |
| 16 | 65,535 |

For example, with only 16 plasmids, 65,535 items of product can be uniquely labeled. It should be appreciated that the segments need not be DNA segments, but also can be RNA segments, segments of other proteins, or other biomolecules. Of importance in the present invention is that each biomolecule or segment differ from one another on the basis of a single trait. These traits include, inter alia, size, molecular weight, density, boiling point, melting point, freezing point, free energy, hydrophobicity, pow (logpow) degree of cooperative or anti-cooperative binding to a ligand, activety, surface tension, shape, sedimentation coefficient, diffusion coefficient, viscosity, absorption of radiation, emmision of radiation, UV spectra, fluorescence, optical rotatory dispersion/circular dichroism, nuclear magnetic resonance, infrared spectra (Foureir transform or any other IR spectra), raman scattering, X-ray emission, X-ray scattering, X-ray diffraction, Bragg reflection of X-rays, electron or neutron diffraction, various parameters of protein folding, and the like. Thus, the power of the present invention lies not only in the secrecy of the location of the mark on the product and the use of multiple markers, but also on which trait of the markers is being used for the identification of source, destination, ect.

Additionally, the biomolecules also could differ from each other by more than one trait. Thus, for example, 2 plasmids may differ from each other by two traits (e.g., size and guanosine-cytosine (GC) content). This two-trait/two-plasmid combination leads to 15 possible combinations while as mere 8 biomolecules differing from each other in 8 traits leads to 65,535 combinations. This is a huge increase in the number of items of product that can aabe marked using fewer biomolecule by ;looking at multiple traits. The power of the present invention is, thus, revealed.

As a chemical method for determining the biologic identifiers, DNA or RNA identifiers can be labeled with biotinylated DATP or dUTP, respectively. To detect their presence on a product, the label can be removed, for example, form a shirt, and the DNA or RNA transferred to a nylon membrane and complexed with streptavidine-alkaline phosphatase. The complex formed, then, is detected by reaction with a chemiluminescent substrate sheet observed on X-ray film.

Just as the sequence of zeros and ones are used by a computer to form a binary code, the four organic bases of DNA (A, adenine; C, cytosine; G, guanine; T, thymine) can be used as a quaternary code. Combinations of the bases can be made to correspond to numbers and letters of the alphabet or to denote individual words or phrases. Just as the biological information is encoded by the sequence of the four bases along the DNA molecule, any desired information could be encoded by the development of a suitable encryption scheme. One such exemplary scheme is set forth in Table 2 below:

TABLE 2

| DNA Base | Corresponding Alphanumeric |
|---|---|
| C | A |
| G | B |
| T | C |
| AA | D |
| AC | E |
| AG | F |
| AT | G |
| CA | H |
| CC | I |
| CG | J |
| CT | K |
| GA | L |
| GC | M |
| GG | N |
| GT | O |
| TT | P |
| TA | Q |
| TC | R |
| TG | S |
| AAA | T |
| AAC | U |
| AAG | V |
| AAT | W |
| ACC | X |
| ACA | Y |
| ACG | Z |
| A | Space |
| AGT | . |
| AGG | 1 |
| AGA | 2 |
| AGC | 3 |
| AGT | 4 |
| ATT | 5 |
| ATA | 6 |
| ATC | 7 |
| ATG | 8 |
| CAC | 9 |
| CTC | 0 |

In practice, a message would be encoded using a suitable encryption scheme or code, and the corresponding DNA sequence chemically synthesized by one of several commonly used methods. Using one of these methods, it is possible to construct single stranded DNA molecules approximately 80 to 100 base pairs in length. If the message were required to be longer, two different sequences could be made, such that one of their ends could form a double-stranded region. The remaining single stranded regions then could be made double stranded using standard enzymatic methods. In this way, someone versed in the art could form a larger information containing molecule than is possible using chemical synthesis alone. By combining a number of single stranded molecules in this way, a double stranded molecule of theoretically unlimited length could be made.

In order to propagate the information, the double stranded DNA message could be cloned into any of a variety of cloning vectors and hosts that are readily available, or could be constructed by someone versed in this art. The mDNA could be transported as the double stranded DNA, as the DNA ligated to a suitable vector, or in a bacterial or bacteriophage host. Use of the host or the cloned mDNA adsorbed dry to a variety of surfaces as the vehicle for transporting the message could make it virtually impossible to detect by direct methods.

In particular, a bacteria or bacteriophage could be adsorbed to a variety of surfaces and be undetectable until it was grown in a suitable media or host. Selective genetic features could be engineered into the host-vector combination that would make it difficult or impossible to recover unless the right combination of conditions were used. Once the mDNA has been recovered using suitable means, it could be decoded in a number of ways.

The most complete way being determining the actual sequence of the mDNA by one or more of a variety of well-known methods and decoding it according to the encryption scheme that had been used. The other way would be to use a DNA probe to detect the presence of particular sequences. This would require that some knowledge of the sequence of the message be known. This method could be used to determine which of a number of possible alternative messages had been sent. The number of possibilities could be quite large, on the order of hundreds of thousands, as the technology for making and detecting the hybridization of DNA probes is highly developed and, in some instances, is automated.

One product diversion implementation of the foregoing encoding embodiment of the present invention involves the application of the DNA matrix (the matrix being a liquid vehicle, such as, for example, a transparent or opaque ink or other liquid sprayable vehicle) and phosphor via spray application techniques (mechanical, air, airless, air-assisted airless, or the like) with provision for injection of a predetermined DNA sequence (encoded DNA). The spray equipment could be fixed or portable. An exemplary use, for example, would be in the marking of clothing or other product which often is subject to diversion. In order to be able to determine whether the product had been diverted, a known DNA sequence would be injected into the spray of matrix and phosphor so that the specific lot of product, say clothing, could be identified at a later date should its diversion become an issue. The DNA sequence, then, would be changed for different lots simply by varying the DNA sequence injected into the spray equipment. Thus, a technique for uniquely identifying products has been revealed.

The DNA or other biologic marker preferably is encapsulated or microencapsulated in a standard encapsulating medium, e.g., casein, for use in marking an object. Amber or Saran Wrap, for example, may be suitable for encasing biomolecules also. Moreover, the capsule material itself may be biologic in nature. For example, nucleic acid can be used to transform a spore-forming bacteria, such as Bacillus or Clostridium. Heating the spore-forming bacteria produces heat and UV resistant spores with which to protect the nucleic acid identifier. Note, that in this example, the spores also function to mask the nucleic acid identifier since the spore masks UV response traits. The spores used may be conidiospores or endospores. Presently preferred is casein encapsulant which has been cross-linked with itself to provide a shell which is resistant to environmental insults for protection of the DNA therewithin, e.g., plasmids with cloned inserts carrying specific DNA sequences wherein the inserts are all of specific defined lengths. Fatty or lipoidal material, plastics or other polymers, also can be considered as suitable encapsulants provided that they do not adversely interact with the DNA or other biologic medium and can be selectively "opened" to reveal the biologic for analysis (and the phosphor for IR detection). The size of the encapsulated biologic materials desirably is on the order of a few microns in size, but can range on up to a millimeter or so, depending upon its intended use.

Alternatively, the DNA could be bound to magnetic microbeads and the magnetic presence determined, such as is proposed in U.S. Pat. No. 5,360,628, in addition to the use of the phosphors or instead of using the phosphors. For example, DNA which is plasmid in size having a lacZ reporter gene can be bound to a DNA-bindable chemical. Magnetic beads (e.g., 1 $\mu$ size) are coated with lacI repressor protein which will bind the plasmid DNA. Then beads, then, can be coated with saran wrap or amber to protect the plasmid. The coated beads then are affixed to the object to be marked and the saran wrap or amber is removed. A Hall Effect or similar device can be used to detect the magnetic beads on the object. Plasmid DNA can be eluted from the magnetic beads using, for example, IPTG and the plasmid DNA sequenced, if necessary, to identify the object with the known sequence. Reference also is made to Biotechiques, vol. 14, pp 624–629 (1993), the disclosure of which is expressly incorporated herein by reference.

While both up-converting and down-converting phosphors may be used, a particularly useful phosphor is a rare earth oxysulfide, such as selected from those phosphors as described in British patent application 2,258,659 published on Feb. 17, 1993, this disclosure of which is expressly incorporated herein by reference. Such phosphors are described as doped yttrium oxysulphide ($Y_2O_2S$), in which the dopants comprise, by weight of the oxysulphide, 4% to 50% of one or both of erbium (Er) and ytterbium (Yb). The material may comprise 1 to 50 ppm of one or more other lanthanide elements. Erbium and ytterbium may be replaced by thulium (Tm), holmium (Ho), or lutetium (Lu). The material may be in the form of particles whose average size is no more than 20 $\mu$m. Reference also is made to O'Yocom, et al., "Rare-Earth-Doped Oxysulfides for Gallium Arsenide-Pumped Lumines Devices", *Met. Trans.*, (1971), 2(3), 763–767, and Wittke, et al., "Erbium-Ytterbium Double Doped Yttrium Oxide. New Red-Emitting Infrared-Excited Phosphor", *J. Appl. Phys.*, (1972), 43(2), 595–600, the disclosures of which are expressly incorporated herein by reference.

With respect to the phosphor as described above (e.g., gallium oxysulfide), such up-converting phosphors require high (peak power) density photon radiation in order to excite emission. A 10 Hz pulsed LED in the 880 nm region of the spectrum with approximately 50 mW peak power should be suitable therefor. With respect to the detector equipment, a simple illuminator can be used where human perception of a greenish glow to determine the presence of the security phosphor is employed.

Another proposed illuminator/detector could be manufactured from a flashing LED with a very narrow pulse width due to the fact that human perception is unnecessary. Such detector could have an optical filter that blocks IR illumination frequency and passes only the frequency of radiation emitted by the phosphor, i.e., target frequency. Such a detector could be used under high ambient light conditions. Such a detector could be configured as a simple swipe-type reader or could have a hinged or removable gate to expose the phosphor to the LED.

A proposed illuminator/detector/reader could have the ability to read encoded patterns of the embedded phosphor, such as, for example, a bar code. The reading capability can be provided by suitable software, such as bar code reader engines.

As an alternative and/or adjunct to phosphors, luminescent labeling based on the lanthenide ions, samarium (III), europium (III), terbium (III), and dysprosium (III), bound by a chelating agent, could be used as labels for DNA, modified DNA, DNA bases, or other biologic markers. Luminescence from such rare earth ions is generated by exciting the naphthalene group attached to the chelating agent. Thus, light shined on the naphthalene group, which has a long-lived excited state, eventually gives up this excitation energy to the lanthenide ion, which responds by emitting light. Because of the way that the lanthenide ions are linked to naphthalene, a single wavelength of light can excite all four labels, each of them emitting light of a characteristic wavelength. Moreover, the emission bandwidths of the lanthenide ions are narrow, even at room temperature in fluid solution, allowing them to be detected simultaneously with minimum overlap.

Because the lifetimes of the excited states of these ions are relatively long, emission detection can be time-gated, virtually eliminating signals from background sources. Time-gating, for present purposes, comprehends use of a pulsed excitation source which allows a time delay between excitation and detection. Thus, the time delay before detection permits sources of interfering light, such as scattered excitation light, Raman scattering, and impurity fluorescence, to die down before detection is initiated. Another advantage of the lanthenide ions is that they are compatible with both capillary gel electrophoresis, which is considerably faster than conventional sequencing using slab gel electrophoresis, and computer collection and analysis of data.

As another aspect of the present invention, the biologic marker used to identify the product can be masked to be virtually undetectable by an observer who has no knowledge of the traits of the biomolecule which is associated with the product as its identifier. For example, a mask set of polypeptides can be added to a sequence of amino acids or nucleotides of a polypeptide (or protein). The counterfeiter, thief, or diverter will not easily be able to determine which molecule is the identifier from the combination of the mask molecules and the identifier molecule. Thus, the set of identifiers may differ from each other by a trait which is different than the trait which distinguishes the set of mask molecules. Alternatively, the mask biomolecule can include molecules which each differ in a trait which is the same trait as the identifier biomolecule, wherein not all members of the mask set have the same magnitude as all members of the identifier set.

The biological mask also can be less tailored to the first identifier, such as, for example, by including junk DNA such as, for example, salmon sperm DNA or calf thymus DNA. For a counterfeiter, thief, or diverter to discern a small concentration of the identifier biomolecule in a large concentration of junk DNA would be expensive, not unlike looking for the proverbial needle in haystack.

By analogy, the other markers of the present invention also can be masked. For example, magnetic identifiers can be masked by one or more magnetic insulators, such as magnetic garnet—for example, gadolinium iron garnet (GdIG) or yttrium iron garnet (YIG) and derivatives and analogs thereof. An optical mask may consist of glass, sand, or another anisotropic material whose function is to provide light of multiple frequencies in order that the presence of the optical identifier is undetectable. Thus, the inventive masking technique has broad application in accordance with the precepts of the present invention.

In the product diversion and anti-counterfeiting fields, products intended for a particular destination will have a particular biologic characterized and the destination will have possession of such characteristics. Upon receipt of the goods, the authorized destination will decode the biologic, for example, to verify a match of those characteristics. Such matching of characteristics or traits can be performed with the aid of a computer, as those skilled in this field will appreciate. Counterfeit goods, of course, will either lack the label or will have a counterfeit label which lacks correspondence with the authentic traits of the biologic, wavelength of IR, etc.

It will be observed that the present invention has apparent utility in a wide variety of fields beyond those described herein. The disclosure herein illustrates the presently-known preferred embodiments for utilizing the labeling technique of the present invention. It will be readily apparent to those skilled in the art that a wide variety of other objects may be suitably labeled in accordance with the precepts of the present invention for their identification and/or verification. Such additional objects and circumstances are included within the scope of the present invention in accordance with the precepts thereof. All citations referred to herein are incorporated expressly herein by reference.

We claim:

1. A method for labeling an object for its identification, which comprises the steps of:

(a) encapsulating with an encapsulant a biologic marker labeled with an agent that emits selected detectable wavelengths of energy when exposed to infrared radiation (IR); and (b) associating said labeled marker with said object, whereby, the object to be identified can be exposed to IR and emitted select wavelengths of energy from said agent detected.

2. The method of claim 1, wherein said biologic marker is identified also.

3. The method of claim 1, wherein said agent is an up-converting phosphor.

4. The method of claim 1, wherein said agent is a lanthenide ion bound to a napthalene group.

5. The method of claim 4, wherein said lanthenide ion is selected from the group consisting essentially of samarium (III), europium (III), terbium (III), dysprosium (III), and mixtures thereof.

6. The method of claim 1, wherein said biologic marker is encoded.

7. The method of claim 6, wherein said biologic marker is formed from encoded DNA bases.

8. The method of claim 1, wherein said biologic marker is one or more of a protein, a nucleic acid sequence, an antibody, a polypeptide, or an antigen.

9. The method of claim 1, wherein said encapsulant is casein which has been cross-linked with itself.

10. The method of claim 1, wherein said capsules also contain one or more of a biologic mask or an optical mask.

11. The method of claim 1, wherein said capsules also contain one ore more of a magnetic marker or a masked magnetic marker.

12. A marker for use in labeling and identifying objects, which comprises:

capsules formed from an encapsulant which encapsulates a biologic marker which marker is labeled with an agent that emits selected detectable wavelengths of energy when exposed to infrared radiation (IR).

13. The marker of claim 12, wherein said agent is an up-converting phosphor.

14. The marker of claim 12, wherein said agent is a lanthenide ion bound to a napthalene group.

15. The marker of claim 12, wherein said lanthenide ion is selected from the group consisting essentially of samarium (III), europium (III), terbium (III), dysprosium (III), and mixtures thereof.

16. The marker of claim 12, wherein said biologic marker comprises encoded DNA bases.

17. The marker of claim 16, wherein said encoded DNA bases is encoded with information to determine the place of origin of an object to which the label is affixed.

18. The marker of claim 12, which is dispersed in a liquid matrix for spray application onto an object to be labeled.

19. The marker of claim 12, wherein said encapsulant is casein which has been cross-linked with itself.

20. The marker of claim 12, wherein said capsules range in size from about 1 micron to about 1 millimeter.

21. The marker of claim 12, wherein said capsules also contain a mask.

22. The marker of claim 12, wherein said biologic marker comprises MHC.

23. A method for labeling an object for its identification, which comprises the steps of:

(a) providing an MHC biologic marker labeled with an agent that emits selected detectable wavelengths of energy when exposed to infrared radiation (IR); and (b) associating said labeled marker with said object, whereby, the object to be identified can be exposed to IR and emitted select wavelengths of energy from said agent detected.

* * * * *